(12) United States Patent
Mucha et al.

(10) Patent No.: US 12,194,262 B2
(45) Date of Patent: Jan. 14, 2025

(54) BALLOON DILATION DEVICE

(71) Applicant: Intersect ENT International GmbH, Hennigsdorf (DE)

(72) Inventors: Dirk Mucha, Glienicke/Nordbahn (DE); Kai Desinger, Berlin (DE); Nicholas Norman, Charlotte, NC (US)

(73) Assignee: Fiagon GMBH, Hennigsdorf (DE)

( * ) Notice: Subject to any disclaimer, the term of this patent is extended or adjusted under 35 U.S.C. 154(b) by 0 days.

(21) Appl. No.: 17/516,580

(22) Filed: Nov. 1, 2021

(65) Prior Publication Data
US 2022/0047854 A1 Feb. 17, 2022

Related U.S. Application Data

(63) Continuation of application No. PCT/EP2020/062083, filed on Apr. 30, 2020.
(Continued)

(30) Foreign Application Priority Data

Aug. 19, 2019 (EP) ..................................... 19192372

(51) Int. Cl.
*A61M 29/02* (2006.01)
*A61B 5/00* (2006.01)
*A61B 5/06* (2006.01)

(52) U.S. Cl.
CPC ............. *A61M 29/02* (2013.01); *A61B 5/065* (2013.01); *A61B 5/6853* (2013.01);
(Continued)

(58) Field of Classification Search
CPC .......... A61M 29/02; A61M 2205/3317; A61M 2205/3327; A61M 2205/587;
(Continued)

(56) References Cited

U.S. PATENT DOCUMENTS 5,209,732 A   5/1993  Lampropoulos et al.
5,562,619 A  10/1996  Mirarchi et al.
           (Continued)

FOREIGN PATENT DOCUMENTS

CN   102458497 A   5/2012
CN   102458555 A   5/2012
           (Continued)

OTHER PUBLICATIONS

Croix et al., Genes expressed in human tumor endothelium, Science, Aug. 18, 2000, pp. 1197-1202, vol. 289.
(Continued)

*Primary Examiner* — Theodore J Stigell
(74) *Attorney, Agent, or Firm* — Nancy C. Wilker

(57) ABSTRACT

The invention related to a balloon dilation device having a distal end and a proximal end. The balloon dilation device comprises a handle, a shaft, an inflatable balloon and at least one sensor coil. The handle extends from the proximal end of the balloon dilation device towards the distal end of the balloon dilation device. The shaft extends from the distal end of the balloon dilation device towards the proximal end of the balloon dilation device, said shaft having an inflation lumen. The inflatable balloon is fixedly arranged at the shaft. The balloon is fluidly connected to the inflation lumen such that the balloon can be inflated and deflated by feeding a fluid through the inflation lumen into the balloon. The at least one sensor coil is arranged at the shaft. The at least one sensor coil is configured for capturing an electromagnetic field and for providing a sensor coil signal representing position and orientation of the sensor coil.

15 Claims, 9 Drawing Sheets

Related U.S. Application Data

(60) Provisional application No. 62/888,631, filed on Aug. 19, 2019, provisional application No. 62/844,922, filed on May 8, 2019, provisional application No. 62/842,025, filed on May 2, 2019.

(52) U.S. Cl.
    CPC ............... *A61M 2205/3317* (2013.01); *A61M 2205/3327* (2013.01); *A61M 2205/587* (2013.01); *A61M 2210/0618* (2013.01)

(58) Field of Classification Search
    CPC ...... A61M 2210/0618; A61M 25/0127; A61M 25/10; A61M 2210/065; A61M 2210/0675; A61M 2210/0681; A61B 5/065; A61B 5/6853; A61B 2034/105; A61B 2034/2051; A61B 2090/3966; A61B 17/24; A61B 34/20; A61B 5/062
    See application file for complete search history.

(56) References Cited

U.S. PATENT DOCUMENTS

| | | | |
|---|---|---|---|
| 5,702,754 | A | 12/1997 | Zhong |
| 6,329,386 | B1 | 12/2001 | Mollison |
| 6,533,772 | B1 | 3/2003 | Sherts et al. |
| 7,105,013 | B2 | 9/2006 | Durcan |
| 7,559,925 | B2 | 7/2009 | Goldfarb et al. |
| 7,717,933 | B2 | 5/2010 | Becker |
| 7,740,642 | B2 | 6/2010 | Becker |
| 7,753,929 | B2 | 7/2010 | Becker |
| 7,771,409 | B2 | 8/2010 | Chang et al. |
| 7,803,150 | B2 | 9/2010 | Chang et al. |
| 8,100,933 | B2 | 1/2012 | Becker |
| 8,142,422 | B2 | 3/2012 | Makower et al. |
| 8,414,473 | B2 | 4/2013 | Jenkins et al. |
| 8,777,926 | B2 | 7/2014 | Chang et al. |
| 8,801,662 | B2 | 8/2014 | Manish et al. |
| 8,858,586 | B2 | 10/2014 | Chang et al. |
| 8,905,922 | B2 | 12/2014 | Makower et al. |
| 9,138,569 | B2 | 9/2015 | Edgren et al. |
| 9,381,328 | B2 | 7/2016 | Xie et al. |
| 9,471,850 | B2 | 10/2016 | Krueger et al. |
| 9,554,817 | B2 | 1/2017 | Goldfarb et al. |
| 9,603,506 | B2 | 3/2017 | Goldfarb et al. |
| 10,022,525 | B2 | 7/2018 | Hanson |
| 10,105,315 | B2 | 10/2018 | Meltzer |
| 10,166,369 | B2 | 1/2019 | Jenkins et al. |
| 10,238,846 | B2 | 3/2019 | Ressemann |
| 10,441,757 | B2 | 10/2019 | Kaufman et al. |
| 10,524,814 | B2 | 1/2020 | Chang et al. |
| 10,603,473 | B2 | 3/2020 | Kaufman et al. |
| 10,688,289 | B2 | 6/2020 | Finson et al. |
| 10,814,108 | B2 | 10/2020 | Kaufman et al. |
| 2002/0082584 | A1 | 6/2002 | Rosenman et al. |
| 2006/0004286 | A1* | 1/2006 | Chang .................. A61B 90/16 606/198 |
| 2006/0004323 | A1* | 1/2006 | Chang .................. A61F 2/186 604/28 |
| 2007/0250105 | A1 | 10/2007 | Ressemann et al. |
| 2008/0065011 | A1 | 3/2008 | Marchand et al. |
| 2009/0082368 | A1 | 3/2009 | Vohra et al. |
| 2009/0163890 | A1 | 6/2009 | Clifford et al. |
| 2009/0226502 | A1 | 9/2009 | Chen |
| 2010/0113939 | A1* | 5/2010 | Mashimo ........ A61M 25/10187 600/488 |
| 2010/0198190 | A1 | 8/2010 | Michal et al. |
| 2010/0198191 | A1 | 8/2010 | Clifford et al. |
| 2010/0211007 | A1 | 8/2010 | Lesch, Jr. et al. |
| 2010/0272773 | A1 | 10/2010 | Kangas et al. |
| 2010/0274188 | A1 | 10/2010 | Chang et al. |
| 2011/0144577 | A1 | 6/2011 | Stankus et al. |
| 2012/0143132 | A1 | 6/2012 | Orlowski |
| 2012/0150142 | A1 | 6/2012 | Weber et al. |
| 2013/0053947 | A1 | 2/2013 | Kangas et al. |
| 2013/0066358 | A1 | 3/2013 | Nalluri et al. |
| 2013/0142834 | A1 | 6/2013 | Esfand et al. |
| 2014/0046255 | A1 | 2/2014 | Hakimimehr et al. |
| 2014/0073911 | A1 | 3/2014 | Munrow et al. |
| 2014/0074140 | A1 | 3/2014 | Johnson et al. |
| 2014/0100445 | A1 | 4/2014 | Stenzel et al. |
| 2014/0200443 | A1 | 7/2014 | Chang et al. |
| 2015/0065810 | A1 | 3/2015 | Edgren et al. |
| 2015/0112134 | A1 | 4/2015 | Suehara et al. |
| 2015/0142046 | A1 | 5/2015 | Andersen et al. |
| 2015/0182732 | A1 | 7/2015 | Zeng et al. |
| 2015/0273117 | A1 | 10/2015 | Wang |
| 2016/0045718 | A1 | 2/2016 | Pruitt et al. |
| 2016/0121088 | A1 | 5/2016 | Fox et al. |
| 2016/0144158 | A1 | 5/2016 | Abbate |
| 2016/0287342 | A1 | 10/2016 | Jacobsen et al. |
| 2017/0028112 | A1 | 2/2017 | Drontle et al. |
| 2017/0165064 | A1 | 6/2017 | Nyuli et al. |
| 2018/0036009 | A1 | 2/2018 | Zoabi et al. |
| 2018/0296811 | A1 | 10/2018 | Chan |
| 2018/0344202 | A1 | 12/2018 | Bar-Tal |
| 2019/0160266 | A1 | 5/2019 | Ngo-Chu et al. |
| 2020/0230373 | A1 | 7/2020 | Stankus et al. |
| 2020/0276422 | A1 | 9/2020 | Finson et al. |
| 2020/0391013 | A1 | 12/2020 | Kaufman et al. |

FOREIGN PATENT DOCUMENTS

| | | |
|---|---|---|
| DE | 10 2011 119 073 A1 | 5/2013 |
| EP | 0691663 A1 | 1/1996 |
| JP | H-8-317970 A | 12/1996 |
| JP | 2008-099917 A | 5/2008 |
| JP | 2011-528275 A | 11/2011 |
| JP | 2013-515591 A | 5/2013 |
| JP | 2014-200269 A | 10/2014 |
| WO | WO-2006/107957 | 10/2006 |
| WO | WO-2010/009335 A1 | 1/2010 |
| WO | WO-2010/121840 A2 | 10/2010 |
| WO | WO-2010/121840 A3 | 10/2010 |
| WO | WO-2010/126912 A1 | 11/2010 |
| WO | WO 2010/132648 A1 | 11/2010 |
| WO | WO-2011/082139 A1 | 7/2011 |
| WO | WO-2013/130464 A1 | 9/2013 |
| WO | WO-2014/066085 A1 | 5/2014 |
| WO | WO-2014/075513 A1 | 5/2014 |
| WO | WO-2016/118923 A1 | 7/2016 |
| WO | WO-2020/221882 A1 | 11/2020 |

OTHER PUBLICATIONS

European Patent Office, Extended European Search Report for EP Application No. 16 740 876.4, Dec. 5, 2018, 6 pages.
European Patent Office, International Search Report and Written Opinion for PCT/EP2020/062083, Aug. 7, 2020, 14 pages.
Sangolkar, et al., Particle size determination of nasal drug delivery system: A review, Int. J. Pharm. Sci. Rev. Res., 2012, pp. 66-73, vol. 17, No. 1.
Savjai et al., Drug Solubility: Importance and Enhancement Techniques ISRN Pharmaceutics, 2012.
The United States Patent and Trademark Office, Non-Final Office Action for U.S. Appl. No. 15/004,807, filed Dec. 31, 2018, 9 pages.
The United States Patent and Trademark Office, Final Office Action for U.S. Appl. No. 15/004,807, filed Apr. 11, 2019, 11 pages.
The United States Patent and Trademark Office, Notice of Allowance for U.S. Appl. No. 15/004,807, filed Jul. 17, 2019, 7 pages.
The United States Patent and Trademark Office, Non-Final Office Action for U.S. Appl. No. 16/436,363, filed Aug. 30, 2019, 8 pages.
The United States Patent and Trademark Office, Final Office Action for U.S. Appl. No. 16/436,363, filed Jan. 14, 2020, 5 pages.
The United States Patent and Trademark Office, Notice of Allowance for U.S. Appl. No. 16/436,363, filed Feb. 27, 2020, 5 pages.
The United States Patent and Trademark Office, Non-Final Office Action for U.S. Appl. No. 16/745,110, filed May 1, 2020, 10 pages.
The United States Patent and Trademark Office, Final Office Action for U.S. Appl. No. 16/745,110, filed Aug. 28, 2020, 12 pages.

(56) References Cited

OTHER PUBLICATIONS

The United States Patent and Trademark Office, Non-Final Office Action for U.S. Appl. No. 16/745,110, filed Feb. 11, 2021, 14 pages.
The United States Patent and Trademark Office, Final Office Action for U.S. Appl. No. 16/745,110, filed May 25, 2021, 16 pages.
The United States Patent and Trademark Office, Non-Final Office Action for U.S. Appl. No. 16/745,110, filed Feb. 17, 2022, 12 pages.
The United States Patent and Trademark Office, International Search Report and Written Opinion for PCT/US2016/014622, Mar. 31, 2016, 9 pages.
The International Bureau of Wipo, International Preliminary Report on Patentability for PCT Application No. PCT/US2016/014622, Jul. 25, 2017, 8 pages.
The United States Patent and Trademark Office, International Search Report and Written Opinion for PCT Application No. PCT/US2019/036506, Aug. 28, 2019, 15 pages.
The United States Patent and Trademark Office, International Search Report and Written Opinion for PCT Application No. PCT/US2020/014090, Apr. 7, 2020, 10 pages.
The United States Patent and Trademark Office, Notice of Allowance mailed on Nov. 22, 2019, for U.S. Appl. No. 16/523,836, filed Jul. 26, 2019, 7 pages.
The United States Patent and Trademark Office, Non-Final Office Action for U.S. Appl. No. 16/790,464, filed Mar. 20, 2020, 5 pages.
The United States Patent and Trademark Office, Corrected Notice of Allowability for U.S. Appl. No. 16/790,464, filed Sep. 29, 2020, 4 pages.

\* cited by examiner

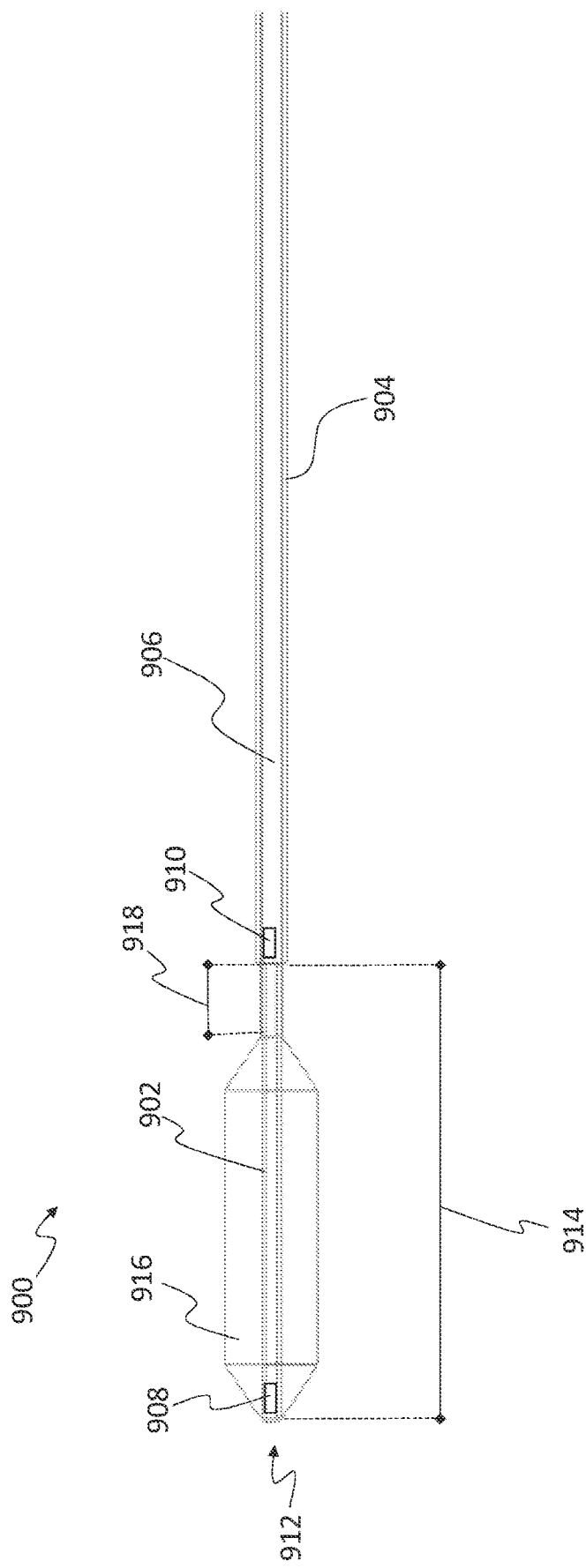

BALLOON DILATION DEVICE

CROSS-REFERENCE TO RELATED APPLICATIONS

This application is a continuation of International Patent Application No. PCT/EP2020/062083 filed on Apr. 30, 2020, which claims priority to U.S. Provisional Patent Application Nos. 62/888,631 filed on Aug. 19, 2019, 62/844,922 filed on May 8, 2019, and 62/842,025 filed on May 2, 2019. International Patent Application No. PCT/EP2020/062083 also claims priority to European Patent Application No. 19192372.1 filed on Aug. 19, 2019. Each of the foregoing disclosures is hereby incorporated by reference in its entirety.

TECHNICAL FIELD

The invention relates to a balloon dilation device, a medical system comprising a balloon dilation device and a method for determining position and orientation of a balloon dilation device.

BACKGROUND OF THE INVENTION

Balloon dilation refers to the dilation of a cavity or passageway of a human body with a balloon.

By way of example, the human skull comprises a group of four paired air-filled spaces known as paranasal sinuses that surround the nasal cavity. Each of the paranasal sinuses opens into the nasal cavity via small orifices.

Normal drainage of mucus from these paranasal sinuses can be interrupted or even become blocked which can result in an infection of the mucus membrane known as sinusitis.

Sinusitis can be treated, e.g., by means of balloon sinuplasty. Sinuplasty often includes using a balloon over-a-wire catheter to dilate sinus passageways to restore the normal drainage. Typically, in sinuplasty a flexible guide wire is inserted through the nostril and guided to a sinus cavity. For correct placement of the guide wire in the sinus cavity, often guide wires are used that have a light source at their tip for emitting light that can be seen by a surgeon through the patient's skin. The surgeon can thus follow the guide wire tip through the skin of a patient. After positioning of the guide wire, a balloon catheter is advanced over the guide wire and positioned in the blocked sinus cavity. When the balloon catheter is positioned in the sinus cavity, its balloon is inflated to dilate the sinus openings and to restore normal drainage.

Balloon catheters that include a movable shaft and methods for treating a sinus cavity of a subject with such a balloon catheter are described inter alia in U.S. Pat. No. 10,022,525 B2 and US 2017/0028112 A1.

A passageway in the human skull that can be dilated with a balloon is the Eustachian tube which links the nasopharynx to the middle ear. Normally, the Eustachian tube is closed, however, it can open, e.g., during swallowing. In its open state the Eustachian tube can provide pressure equalization between the middle ear and the atmosphere. Another function of the Eustachian tube is to drain mucus from the middle ear. The function of the Eustachian tube can be disrupted, e.g., by swelling or by blockage, e.g., as a result of a cold or allergies. If the function of the Eustachian tube is disrupted, e.g., caused by a disease of the middle ear such as otitis media, the Eustachian tube can be dilated with a balloon of a balloon dilation catheter to restore normal drainage and to achieve pressure equalization.

A method for dilating a Eustachian tube of a patient with a dilation device is described, e.g., in US 2010/0274188 A1. A device including a guide catheter and a balloon dilation catheter for dilating a Eustachian tube of a patient is disclosed in US 2018/0296811 A1.

SUMMARY OF THE INVENTION

It is an object to provide an improved balloon dilation device, to provide an improved medical system comprising a balloon dilation device and to provide an improved method for determining position and orientation of a balloon dilation device.

Regarding the balloon dilation device, the object is achieved by a balloon dilation device having a distal end and a proximal end. The balloon dilation device comprises a handle, a shaft, an inflatable balloon and at least one sensor coil. The handle extends from the proximal end of the balloon dilation device towards the distal end of the balloon dilation device. The shaft extends from the distal end of the balloon dilation device towards the proximal end of the balloon dilation device, said shaft having an inflation lumen. The inflatable balloon is fixedly arranged at the shaft. The balloon is fluidly connected to the inflation lumen such that the balloon can be inflated and deflated by feeding a fluid through the inflation lumen into or out of the balloon. The at least one sensor coil is arranged at the shaft. The at least one sensor coil is configured for capturing an electromagnetic field and for providing a sensor coil signal representing position and orientation of the sensor coil.

The balloon dilation device according to the invention is suitable for dilating a sinus cavity and the Eustachian tube of a patient. The balloon dilation device does not need to be modified in order to dilate either a sinus cavity or a Eustachian tube. For dilating a sinus cavity or for dilating a Eustachian tube, the balloon dilation device can be inserted through the nostril of a patient and guided to either the sinus cavity or a Eustachian tube.

The invention includes the recognition that a balloon dilation device such as a balloon catheter has to be guided through the human body in minimal invasive surgery and positioned in a sinus cavity before inflating the balloon. For positioning the balloon dilation device in a sinus cavity, commonly, first, a guide wire has to be inserted into the human body over which, in a second step, the balloon dilation device is advanced. A typical guide wire used in sinuplasty has a light source at its tip. To find the sinus cavity with the guide wire, the surgeon, typically, has to rely on a light spot as seen from outside through the skin. Thus, the surgeon cannot follow the guide wire or balloon dilation device inside the human body while guiding the guide wire or balloon dilation device.

Since the balloon dilation device according to the invention is equipped with at least one sensor coil, position and orientation of the balloon dilation device in relation to a human body can be determined by means of an electromagnetic position detection system. For determining position and orientation of the balloon dilation device, position and orientation of the at least one sensor coil are determined with the position detection system. Based on the determined position and orientation of the at least one sensor coil, position and orientation of the balloon dilation device can be calculated. With a position detection system, positions of the at least one sensor coil can be determined while moving the at least one sensor coil relative to, e.g., a field generator generating an electromagnetic field. From repeatedly determined positions of the at least one sensor coil, positions of the balloon dilation device moved relative to a position detection system can be determined and, thus, the position of the balloon dilation device can be tracked while guiding the balloon dilation device.

For example, for determining position and orientation of the at least one sensor coil, an electromagnetic position detection system can be used that comprises a field generator for generating an alternating electromagnetic field.

When exposing the balloon dilation device equipped with the at least one sensor coil to an alternating electromagnetic field, a current is induced in the at least one sensor coil. The current induced in the at least one sensor coil depends on the position and orientation of the sensor coil in the alternating electromagnetic field. Thus, from a sensor coil signal representing the induced current, position and orientation of the at least one sensor coil can be determined. When knowing the spatial relation between the balloon dilation device and the at least one sensor coil, e.g., the relative distance from the distal end of the balloon dilation device to the at least one sensor coil, position and orientation of the balloon dilation device can be calculated by a position detection system based on the detected position and orientation of the at least one sensor coil.

For supporting a surgeon in navigating the balloon dilation device, e.g., inside a patient's body, position and orientation of the balloon dilation device equipped with at least one sensor coil can be detected by means of such a position detection system and the position of the balloon dilation device can be displayed in sectional images of a patient's body part obtained, e.g., by tomography. Thus, the surgeon using the balloon dilation device according to the invention can follow the position of the balloon dilation device inside a human body on a monitor displaying sectional images and a digital representation of the balloon dilation device while guiding the balloon dilation device through the human body. Advantageously, a surgeon can adapt the way of the moving the balloon dilation device, e.g., an applied pressure or an angle of the balloon dilation device to a body part, according to the determined actual position and orientation of the balloon dilation device inside the human body.

Advantageously, since position and orientation of the balloon dilation device equipped with at least one sensor coil can be directly tracked with a position detection system, initially using a guide wire for finding a cavity becomes obsolete. Thus, with the balloon dilation device according to invention the number of steps necessary to position a balloon dilation device in a balloon cavity can be reduced and likewise surgery time can be saved.

In the following preferred embodiments of the balloon dilation device according to the invention are described.

Within the framework of this specification a fluid can be a gas or a liquid. Thus, for inflating the balloon either a gas, e.g., air, can be fed into the balloon through the inflation lumen or a liquid can be fed into the balloon through the inflation lumen. When inflating the balloon, balloon and inflation lumen are in fluid communication. Likewise, through the lumen the fluid inside the balloon can be removed, i.e., fed out of the balloon, to deflate the balloon.

It is advantageous if the handle comprises an attachment for attaching a fluid source to the inflation lumen, e.g., via a tube, for feeding a fluid through the inflation lumen into the balloon. The inflation lumen can extend from said attachment for attaching a fluid source through the handle and the shaft up to a connecting point where the balloon is fluidly connected to the inflation lumen.

It is preferred that the balloon is fixedly arranged at the shaft such that the balloon cannot be shifted along the shaft in longitudinal direction.

Preferably, the shaft is attached to the handle. For example, the shaft can extend at least through a part of the handle. The shaft can also extend through the handle along the full length of the handle up to the proximal end of the balloon dilation device.

Preferably, the shaft has a length between 80 mm and 220 mm. It can be advantageous if the shaft has a length that is between 90 mm and 180 mm. For various applications it is beneficial if shaft has a length that is between 110 mm and 140 mm, e.g., 130 mm. The shaft length refers to the distance between the distal end of the balloon dilation device and the distal end of the handle and, thus, refers to the visible part of the shaft.

In particular, the shaft can have an outer diameter between 1.2 mm and 1.8 mm. It is advantageous if the shaft has an outer diameter that is between 1.2 mm and 1.6 mm. For various applications it is beneficial if the shaft has an outer diameter that is between 1.2 mm and 1.4 mm. It is possible that the shaft has various sections, the sections having different outer diameters. For example, if the shaft has a malleable tip region, in the malleable tip region the shaft can have an outer diameter that is smaller than the outer diameter of the rest of the shaft. The shaft can be made of one piece, e.g., one hypo tube. It is also possible that the shaft comprises different pieces, e.g., two hypo tubes having different outer diameters that are chosen such that one hypo tube can be arranged at last partly inside the lumen of the other hypo tube.

A shaft with the dimensions specified above is suitable for being inserted into a nostril and guided to a sinus cavity or a Eustachian tube also with a deflated balloon being arranged at the shaft.

The shaft can comprise at least one hypo tube that is made of, e.g., polytetrafluoroethylene (PTFE), steel or nitinol. Typically, a hypo tube is a long metal tube with micro-engineered features along its length that shall provide the desired mechanical properties of the hypo tube. If the shaft comprises more than one hypo tube, the hypo tubes can be made of different materials.

It is preferred that the shaft is configured such that external forces as to be expected during use of the balloon dilation device do not cause a plastic deformation of the shaft. Accordingly, the shaft shall not deform plastically when exposed to external forces having a magnitude typically occurring when the shaft is inserted into a cavity or passageway. However, the shaft can be configured such that it deforms elastically when an external force typically occurring during surgery is exerted on the shaft. In this case, after release of the force the shaft returns to its rest position.

The handle, preferably, has a length that is between 100 mm and 200 mm, preferably, between 120 mm and 130 mm. For various applications it is advantageous if the shaft and the handle have a similar length.

From its distal end to its proximal end the balloon dilation device can have a total length that is between 180 mm and 440 mm. However, it is preferred that the total length of the balloon dilation device is between 200 mm and 300 mm.

It is particularly preferred that the shaft has a malleable tip region extending from a distal end of the balloon dilation device towards the proximal end of the balloon dilation device. If the shaft has a malleable tip region the inflatable balloon, preferably, is fixedly arranged at the shaft in the malleable tip region. It is preferred that the balloon is arranged in the malleable tip region adjacent to the distal end of the balloon dilation device.

In particular, a shaft with the dimensions (length and diameter) as specified above can have a malleable tip region extending from a distal end of the balloon dilation device towards the proximal end of the balloon dilation device in which the balloon is fixedly arranged.

The malleable tip region can have a length of between 10 mm and 60 mm. It is advantageous if the length of the malleable tip region is between 20 mm and 50 mm. In various embodiments, the malleable tip region has a length of between 25 mm and 35 mm, e.g. 30 mm. The length of the malleable tip region is included into the length of the shaft and, thus, does not add to the shaft length. In particular, in the malleable tip region, the shaft can have an outer diameter that is smaller than the outer diameter in the rest of the shaft.

The malleable tip region can be produced, e.g., by treating the shaft with heat. For example, if the shaft comprises a hypo tube that is made of steel, the shaft can be annealed at its distal end for fabricating the malleable tip region. For example, if the shaft is made of one piece, the shaft can be annealed in a selected region, e.g., in a region adjacent to the tip of the balloon dilation device, to produce the malleable tip region.

That the shaft can comprise a completely annealed inner hypo tube and an outer hypo tube. The inner hypo tube can be at least partly arranged inside a lumen of the outer hypo tube. Thus, the inner hypo tube can extend only partly into the lumen of the outer hypo tube or can extend along the full length of the outer hypo tube. Preferably, the outer hypo tube is attached to the handle.

Preferably, the length of the outer hypo tube is shorter than the total length of the shaft. In particular, it is preferred that the outer hypo tube ends before the distal end of the balloon dilation device. In case the outer tube ends before the distal end of the balloon dilation device it is preferred that at least a part of the inner hypo tube extends from the distal end of the outer hypo tube to the distal end of the balloon dilation device. Thus, the total length of the shaft is the sum of the lengths of the visible parts of the inner and outer hypo tubes.

That part of the inner hypo tube that extends from the distal end of the outer hypo tube to the distal end of the balloon dilation device, i.e., the visible part of the inner hypo tube, preferably, forms the malleable tip region of the shaft. An advantage of a shaft that comprises an inner hypo tube that is completely annealed and an outer hypo tube that is configured to not to deform plastically under an external force typically acting on the shaft when being guided through the human body is, that the length of the malleable tip region can be designed with high accuracy. Thus, the starting point of the malleable tip region can be selected and implemented very accurately.

In case the shaft comprises an inner and an outer hypo tube, the balloon of the balloon dilation device, preferably, is attached to the inner hypo tube, only.

After annealing, i.e., after heat treatment, the malleable tip region of the shaft, preferably, is made from a material having an ultimate tensile strength of up to 750 Nmm$^{-2}$. It is also possible that the shaft comprises a different material or material composition in the malleable tip region as in the rest of the shaft. However, it is preferred that the shaft is made of only one material or material composition and that the malleable tip region is produced by heat treatment of the shaft in that region.

Preferably, in the malleable tip region the shaft can be deformed plastically without modifying the shape of the rest of the shaft. Thus, the shape of the malleable tip region of the shaft can be designed in a way that is suitable for surgery with the balloon dilation device. For example, it is preferred that an angle is formed in the malleable tip region of the shaft. Accordingly, the tip of the shaft can be arranged at an angle with respect to the rest of the shaft. During surgery, the shaft can be rotated to position the tip of the shaft at an angle suitable for entering a certain passageway, e.g. a passageway branching off a first passageway.

For plastically shaping the malleable tip region of the shaft and, thus, for implementing a new rest position of the malleable tip region, an external force can be exerted on the malleable tip region of the shaft that is sufficient to deform the malleable tip region of the shaft plastically.

Preferably, the amount of external force required to be exerted at the malleable tip region of the shaft in order to change the malleable tip region shape with respect to the rest of the shaft, still, is greater than a force that typically acts on the shaft during insertion into the sinuses. Thus, after the malleable tip region of the shaft is formed into the desired shape, the malleable tip region will not plastically change shape during insertion into the desired sinus cavity. Elastic deformation of the malleable tip region may occur, however, while using the device.

If the malleable tip region of the shaft can only be deformed when an external force is applied that is larger than forces typically occurring during surgery, while inserting the shaft into a cavity or passageway the malleable tip region of the shaft is deformed elastically, only. Thus, after releasing an external force during surgery the malleable tip region of the shaft returns to its prior defined rest position.

For the plastically shaping of the malleable tip region of the shaft into a desired shape, an external shaping tool can be used. A shaping tool can comprise a region for inserting the malleable tip region of the shaft. Such shaping tool can be used to apply an external force to the malleable tip region of the shaft for shaping of the malleable tip region of the shaft with respect to the rest of the shaft. Preferably, the shaping tool comprises a number of pre-fixed shaping position options for shaping the malleable tip region of the shaft into one of the pre-fixed shapes. Such pre-fixed shape positions can be defined for a suitable angle degree needed for accessing, e.g., particular sinuses, for example, 120-130 degrees bend for accessing the maxillary sinuses, 70-90 degrees bend for accessing the frontal sinuses, and 10-15 degrees for accessing the sphenoid sinuses. The shaping tool, preferably, is designed to take account of potential recoil or spring back due to elastic deformation.

It is preferred that at the distal end of the balloon dilation device the shaft has a rounded and smoothed tip. This advantageous as tissue or other body parts of a human body are less likely to become damaged during surgery with the balloon dilation device.

Preferably, the at least one sensor coil is arranged at the shaft at the distal end or at least close to the distal end of the balloon dilation device. This is preferred since for guiding and positioning the balloon dilation device, typically, the position of the tip of the balloon dilation device has to be determined which can be achieved with high accuracy when the at least one sensor coil is arranged at the distal end of the balloon dilation device. Further, if the shaft comprises a malleable tip, the at least one sensor coil being arranged at the distal end or at least close to the distal end of the balloon dilation device is arranged at that point of the shaft that typically is bend most with respect to the rest of the shaft under an external force.

Preferably, the at least one sensor coil is connected to electrical wiring running up to the proximal end of the balloon dilation device and being configured for transmitting sensor coil signals. The electrical wiring can be connected to a cable, e.g., at an electrical connection, the cable connecting the balloon dilation device to a position detection system.

With one sensor coil, typically, five degrees of freedom can be detected, namely, three translations and two rotations. Based on the detected translations and rotations, position and orientation of the sensor coil can be determined. However, the rotation around the longitudinal axis of a sensor coil cannot not be detected. This sixths degree of freedom can be obtained, e.g., by simultaneously determining position and orientation of a second sensor coil that is arranged at a non-zero angle to the first sensor coil.

In various embodiments, it is of advantage if the balloon dilation device, additionally to the at least one sensor coil, comprises a second sensor coil that is arranged at the shaft. Preferably, the second sensor coil is displaced at a distance in longitudinal direction from the at least one sensor coil. Thus, in a situation when the first sensor coil and the second sensor coil are arranged at a non-zero angle to each other, the respective rotational degree of freedom representing rotations around a respective longitudinal axis of a respective sensor coil can be determined from the position and orientation determined for the respective other sensor coil. For example, two sensor coils can be arranged at the shaft such that after plastically shaping the shaft in its malleable tip region, the respective longitudinal axis of the two sensor coils having a non-zero angle to each other.

The second sensor coil can be displaced in longitudinal direction from the first sensor coil either more towards the tip or more towards the handle.

In various embodiments, it is preferred that the balloon is arranged between the two sensor coils. In particular, it is preferred that—if the shaft has a malleable tip region—the second sensor coil is arranged at the shaft adjacent to the malleable tip region. Thus, when bending the malleable tip region, the second sensor coil does not follow the bending but stays fixed relative to, e.g., the rest of the shaft and the handle. However, the first sensor coil that is arranged in the malleable tip region, e.g., at the distal end of the balloon dilation device, follows the bending and thus changes its angle with respect to the second sensor coil. From the determined position and orientation of the first sensor coil and from the determined position and orientation of the second sensor coil a bending of the shaft in the malleable tip region can be calculated and thus the shape of the shaft in the malleable tip region can be reconstructed and visualized on a monitor.

The balloon dilation device can have a central lumen extending from the distal end of the balloon dilation device towards the proximal end of the balloon dilation device. Preferably, the central lumen extends between the distal end and the proximal end of the balloon dilation device and has a distal opening at the distal end of the balloon dilation device and a proximal opening at the proximal end of the balloon dilation device. In other words, the central lumen, preferably, extends from an opening in the shaft at the distal end of the balloon dilation device to an opening in the handle at the proximal end of the balloon dilation device. At the opening at the proximal end of the balloon dilation device an attachment can be provided, e.g., at the handle for inserting, e.g., a marker carrier equipped with a sensor coil and/or fluoroscopically detectable markers, a light fibre or a suction tube into the central lumen.

Preferably, the central lumen has a diameter between 0.5 mm and 1.0 mm. It can be advantageous if the central lumen has a diameter that is between 0.6 mm and 1.0 mm. In various embodiments it is beneficial if the central lumen has a diameter that is between 0.7 mm and 1.0 mm. The diameter of the central lumen likewise constitutes an inner diameter of the shaft or—if the shaft comprises a hypo tube—an inner diameter of the hypo tube.

The central lumen can be used for various purposes. For example, advantageously a marker carrier can be removably arranged in the central lumen. A marker carrier comprises at least one sensor coil and can thus be used to connect a balloon dilation device to a position detection system. A balloon dilation device whose position and orientation could not be determined with a position detection system before can then be used with a position detection system. A surgeon using the balloon dilation device with a marker carrier can be supported by a position detection system in guiding the balloon dilation device to a cavity inside a human body. After positioning the balloon dilation device in, e.g., a sinus cavity, the marker carrier can be removed and the central lumen can be used for other purposes. A passable lumen can, e.g., be used for suction and irrigation purposes, i.e., for inserting a fluid, e.g. medication, into or removing a fluid from a sinus cavity.

In particular, if the balloon dilation device comprises a central lumen it is preferred that the balloon dilation device comprises a marker carrier that is removably arranged inside and extends along the length of the central lumen. It is further preferred that the marker carrier comprises the at least one sensor coil. When the balloon dilation device is position inside a sinus cavity, the at least one sensor coil sometimes is not needed anymore and can be removed as part of the marker carrier from the central lumen as not to require space in the balloon dilation device. A balloon dilation device with marker carrier can be delivered in calibrated state such that it can be directly used within a position detection system. Calibrating the at least one sensor coil to the distal tip of the balloon dilation device before surgery then is not necessary. For example, calibration data can be fed into and used by a position detection system for determining position and orientation of the balloon dilation device in relation to the position detection system.

For example, a marker carrier that is arranged in the central lumen can be a marker carrier that has a proximal end and a distal end, the marker carrier comprising at least one sensor coil that is configured for capturing an alternating electromagnetic field. Position and orientation of the at least one sensor coil can be determined with a position detection system. The at least one sensor coil is arranged at the distal end of the marker carrier or at least close to the distal end of the marker carrier. Advantageously, the at least one sensor coil is then likewise arranged at the or at least close to the distal end of the balloon dilation device having the marker carrier arranged in its central lumen. Preferably, a distal end region of the marker carrier extends from the distal end of the marker carrier to the proximal end of the at least one sensor coil such that the at least one sensor coil is arranged within the distal end region of the marker carrier. The distal end region of the marker carrier can have the same length as a malleable tip region of the shaft of the balloon dilation device. The distal end region of the marker carrier can also have a smaller length than a malleable tip region of the shaft of the balloon dilation device such that the distal end region of the marker carrier lies within the malleable tip region of the shaft.

Preferably, in the distal end region in which the at least one sensor coil is arranged, the marker carrier has at least in one section a bending stiffness of less than 10 Nmm².

It is also preferred that the at least one sensor coil of the marker carrier is connected to electrical wiring running up to the proximal end of the marker carrier for transmitting sensor coil signals.

The electrical wiring can be connected to an electrical connection located at the proximal end of the marker carrier, the electrical connection serving for connecting the marker carrier to a cable of a position detection system.

Preferably, the at least one sensor coil of the marker carrier has a length that is at least ten times greater than the diameter of the sensor coil. Preferably, the at least one sensor coil has an induction that is between 2 mH and 4 mH.

A marker carrier is an auxiliary device that can be removably arranged in the central lumen of the balloon dilation device for using the balloon dilation device together with a position detection system. Due the marker carrier that is arranged in the central lumen of the balloon dilation device, position and orientation of the balloon dilation device can be determined with a position detection system.

Preferably, the balloon of the balloon dilation device has a length of between 10 mm and 25 mm. It can be advantageous if the balloon has a length that is between 15 mm and 20 mm. In various embodiments a length of 18 mm is preferred.

The balloon can be made, e.g., of polyester or nylon or polyurethanes. For certain applications it is of advantage if the balloon is made of polyurethane or silicone.

Preferably, —when inflated—the balloon has a maximum diameter that is between 3 mm and 10 mm, preferably between 5 mm and 8 mm, even more preferably of 6 mm. It is also preferred that the balloon is configured for holding an inflation pressure of up to 12 atm.

In particular, in various embodiments it is preferred if the balloon is configured for withstanding bending multiple times at angles of up to 120 degrees. This is of particular importance if the balloon is arranged in the malleable tip region of the shaft and thus is exposed to bending of the shaft under an external force.

The balloon dilation device can advantageously be used in balloon sinuplasty. Thus, the balloon dilation device according to the invention can be used for the treatment of blocked sinuses by inflating the balloon inside the human body. Since the balloon dilation device is equipped with at least one sensor coil, position and orientation of the balloon dilation device can be determined with an electromagnetic position detection system while a surgeon guides and positions the balloon dilation device inside a human body. Advantageously, the position of the balloon dilation device can be displayed in sectional images, e.g., of a 3D model, of a patient to assist a surgeon in guiding and positioning the balloon dilation device inside a patient's body.

With regard to the medical system, the aforementioned object is achieved by a medical system comprising a balloon dilation device, a position detection system, a fluid source and a visualization unit comprising a monitor. The balloon dilation device has an inflatable balloon and at least one sensor coil. The position detection system is configured for determining position and orientation of the balloon dilation device based on sensor coil signals provided by the at least one sensor coil of the balloon dilation device. The fluid source is attached to the balloon dilation device for feeding a fluid into the balloon. The visualization unit is configured for visualizing at least a part of the balloon dilation device on a monitor based on the determined position and orientation of the balloon dilation device.

Preferably, the balloon dilation device of the medical system is configured according to one of the embodiments of the balloon dilation device according to the invention as described before.

In particular, it is preferred if the visualization unit is configured for visualizing at least a part of the balloon dilation device on a monitor together with a preoperatively obtained model or images of a body part of a patient. Visualizing at least a part of the balloon dilation device refers to visualizing a digital representation of a part of the balloon dilation device, e.g., the balloon dilation device tip, that can also be visualized as an icon.

The medical system can comprise a device shape reconstruction unit. The device shape reconstruction unit is configured for reconstructing the shape of the balloon dilation device based on position and orientation of the balloon dilation device as determined by the position detection system. The visualization unit, preferably, is configured for visualizing the balloon dilation device in its reconstructed shape. Preferably, the device shape reconstruction unit is configured for reconstructing the shape of the balloon dilation device based on position and orientation determined for at least two sensor coils that are arranged at a relative distance from each other along the shaft of the balloon dilation device. In particular, based on position and orientation determined for at least two sensor coils, the shape of the part of balloon dilation device that lies between the two sensor coils can be reconstructed. If further sensor coils, e.g. a third and a fourth sensor coil are arranged at the shaft it is possible that the accuracy of reconstructing the shape can be improved, e.g., comparable to a spline interpolation. In particular, if the shaft comprises a malleable tip region it is preferred that at least one coil is arranged at the tip, thus, at the distal end of the balloon dilation device. At least a second sensor coil, preferably, is arranged adjacent to the malleable tip region. Under an external force, e.g., exerted by a shaping tool, the malleable tip region is bend such that the first sensor coil is displaced with respect to the second sensor coil. The displacement of the first sensor coil with respect to the second sensor coil yields that the first sensor coil is positioned at a non-zero angle to the second sensor coil with respect to their respective longitudinal axis such that a degree of bending of the part of the shaft that lies between these two sensor coils can be determined and the shape of the shaft in the malleable tip region reconstructed. The determined degree of bending can be used to visualize a digital representation of the balloon dilation device on a monitor taking into account the bending of the shaft as reconstructed with the device shape reconstruction unit.

It is advantage, if the fluid source comprises at least one fluid sensor for measuring a physical quantity of a fluid that is provided by the fluid source for inflating or deflating the balloon. Preferably, the at least one fluid sensor is configured for providing fluid sensor signals representing the measured a physical quantity. In particular, if the fluid source comprises at least one fluid sensor, the medical system, preferably, comprises a balloon shape computation unit.

The balloon shape computation unit is configured for computing the shape of the balloon based on fluid sensor signals provided by the at least one fluid sensor of the fluid source. The fluid sensor can be an inflation pressure sensor for measuring an inflation pressure. The fluid sensor can also be a fluid volume sensor for measuring an amount of fluid that has been fed into the balloon. From the measured inflation pressure and/or the amount of fluid that has been fed into or out of the balloon, the shape of the balloon can be calculated by means of the balloon shape computation unit, in particular, when further taking into account the constraints of the balloon geometry.

In particular, if the medical system comprises a balloon shape computation unit it is preferred that the visualization unit is configured for visualizing the balloon dilation device having a balloon shape as computed by the balloon shape computation unit. Thus, the balloon dilation device can be visualized with a balloon in its inflated or deflated state as computed by the balloon shape computation unit.

Regarding the method, the aforementioned object is achieved by a method for determining position and orientation of a balloon dilation device.

The method comprises the steps of generating an electromagnetic field, exposing the balloon dilation device to the electromagnetic field, the balloon dilation device having an inflatable balloon and at least one sensor coil, detecting position and orientation of the at least one sensor coil, determining position and orientation of the balloon dilation device based on the detected position and orientation of the at least one sensor coil, and visualizing at least a part of the balloon dilation device on a monitor based on the determined position and orientation of the balloon dilation device.

Preferably, a digital representation of at least a part of the balloon dilation device, e.g., the device tip, is visualized on a monitor together with images of a patient, e.g., sectional images obtained preoperatively or intraoperatively by tomography. This allows a surgeon to guide the balloon dilation device inside a human body while orienting oneself on the displayed position of the balloon dilation device in respective images of a patient.

Preferably, the method comprises at least one of the steps of calculating future position and orientation of the balloon dilation device with an inflated balloon based on the determined position and orientation of the balloon dilation device with a deflated balloon, or calculating future position and orientation of the balloon dilation device with a deflated balloon based on the determined position and orientation of the balloon dilation device with an inflated balloon.

The determined position and orientation of the balloon dilation device with inflated or deflated balloon can be used to calculate a future position of the balloon dilation device. The calculated future position of the balloon dilation device can be used to visualize the balloon dilation device in a possible future state, e.g., located at a possible future position inside a cavity. Thereby, a surgeon is able to see in advance the outcome of inflating or deflating the balloon of the balloon dilation device at a certain position of the balloon dilation device, e.g., inside a cavity. Additionally, a measured inflation pressure and/or an amount of fluid fed into the balloon as well as the balloon geometry can be taken into account for calculating future positions of the balloon dilation device. A surgeon can thus estimate the consequence of inflating or deflating the balloon at a certain of the balloon dilation device inside, e.g., a sinus cavity. If a surgeon is not convinced of the possible future result, the surgeon can amend the actual position of the balloon dilation device such that a further future position of the balloon dilation device can be calculated starting from this amended actual position of the balloon dilation device.

Additionally or alternatively to the step of calculating possible future positions of the balloon dilation device, the method according to the invention can comprise the step of determining a shape of at least a part of the balloon dilation device based on detected position and orientation of the at least one sensor coil and on detected position and orientation of a second sensor coil that are arranged at a shaft of the balloon dilation device.

Preferably, position and orientation of the first and second sensor coils are determined simultaneously.

Preferably, the second sensor coil is displaced at a distance in longitudinal direction from the at least one sensor coil. It is particularly preferred that if the balloon dilation device comprises a malleable tip region, the at least one sensor coil is arranged at the distal end of the balloon dilation device. When the shaft is bend in the malleable tip region, e.g., using a shaping tool, preferably, the at least one sensor coil arranged in the malleable tip region is displaced with respect to the rest of the shaft. For determining a shape of at least a part of the balloon dilation device and, in particular, of the shaft in the malleable tip region it is therefore preferred that the second sensor coil is arranged at the shaft outside the malleable tip region, preferably, adjacent to the malleable tip region such that the first sensor coil is also displaced with respect to the second sensor coil. The second sensor coil then represents position and orientation of the rest of the shaft that stays unbend and provides a reference for determining the bending of the shaft in its malleable tip region.

Thus, at the time of determining position and orientation of the first and second sensor coils the two sensor coils are arranged at an angle with respect to each other. From position and orientation of the two sensor coils that with the shaft being bend in the malleable tip region are displaced at an angle to each other, the shape of the balloon dilation device with bended shaft can be determined. Preferably, the method then comprises the step of visualizing the balloon dilation device in a shape as determined based on position and orientation of the at least one sensor coil and of the second sensor coil.

Advantageously, this allows a surgeon to see the actual shape of the balloon dilation device having a bend shaft and adapt the use of the balloon dilation device accordingly. If the surgeon can see the balloon dilation device in its actual shape on a monitor, the surgeon can decide more reliably whether or not the actual position in a cavity or passageway is suitable for inflating the balloon.

Optionally, the method can comprise the step of visualizing the shape of the balloon based on an applied inflation pressure and/or based on the amount of fluid that has been fed into the balloon.

A surgeon can thus see the balloon dilation device with inflated balloon in images of a patient. It is also possible to follow the inflation state on a monitor while increasing the inflation pressure and/or the amount of fluid feed into the balloon. Preferably, the 3D shape of balloon is visualized in the 3D model of patient. A 3D model can be generated, e.g., by overlying multiple 2D computer tomography (CT) orthogonal views of a patient.

The method can comprise the step of visualizing a preview of the inflated balloon before actually inflating the balloon based on the determined position and orientation of the balloon dilation device.

A preview of the expanded balloon can be visualized before dilation. Advantageously, a surgeon can estimate whether inflation of the balloon yields the desired effect and if not, change the position of the balloon dilation device.

The balloon dilation device can be used in balloon sinuplasty.

The balloon dilation device can be used for dilating a Eustachian tube.

BRIEF DESCRIPTION OF THE DRAWINGS

In the following, preferred embodiments of the invention are described with respect to the figure. In the figures:

FIG. 9: schematically shows a shaft of a balloon dilation device in a longitudinal sectional view, the shaft comprising an inner and an outer hypo tube.

DETAILED DESCRIPTION

Figure 1:
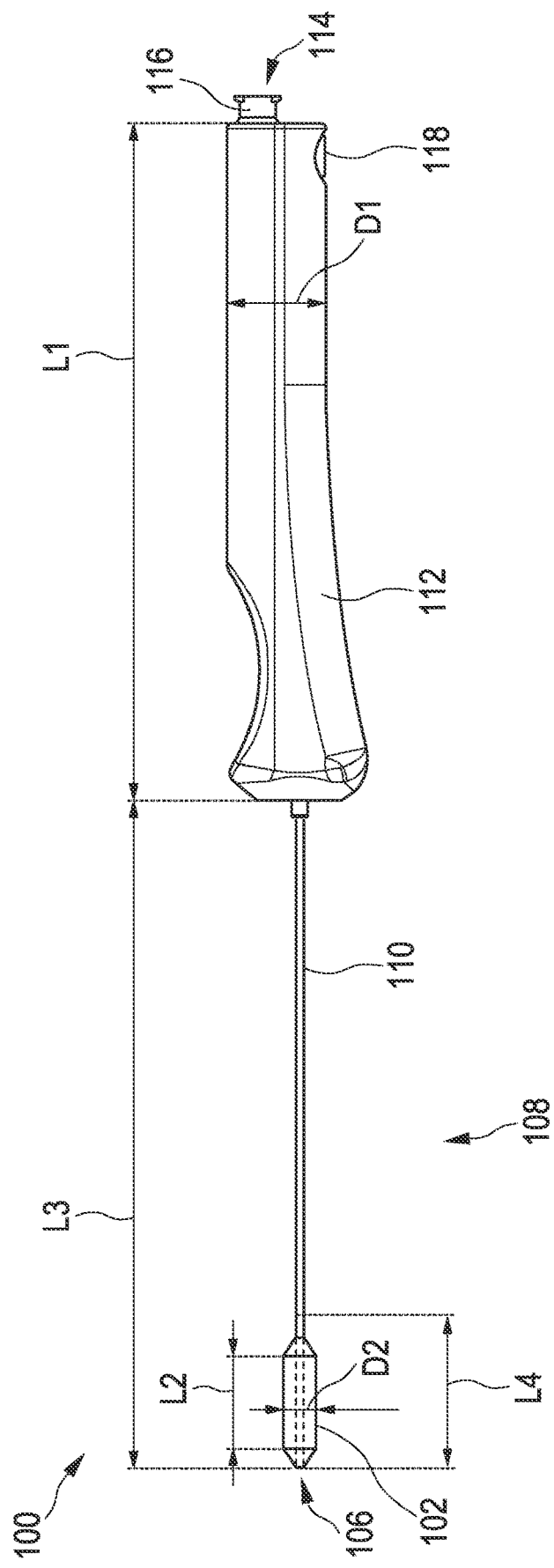
FIG. 1: schematically shows a balloon dilation device having a balloon and a sensor coil arranged at the distal end of the balloon dilation device.

FIG. 1 schematically shows a balloon dilation device 100 having a balloon 102 and a sensor coil (not shown) arranged at the distal end 106 of the balloon dilation device 100.

The balloon dilation device 100 can be used for dilating a sinus cavity and a Eustachian tube.

The balloon dilation device 100 comprises a shaft 108, the shaft 108 comprising a hypo tube 110. The hypo tube 110 can be made of, e.g., polytetrafluoroethylene (PTFE), steel, or nitinol. The hypo tube 110 has an outer diameter of 1.4 mm. In various other embodiments that are not shown the balloon dilation device is realised with a hypo tube having an outer diameter of between 1.2 mm and 1.5 mm. The hypo tube 110 has a central lumen (not visible) having a diameter of 0.8 mm thus constituting an inner diameter of the hypo tube. In various other embodiments that are not shown the balloon dilation device is realised with a hypo tube having an inner diameter of between 0.7 mm and 1.0 mm. Alternatively, the shaft can be realized without a central lumen and with the at least one sensor coil, e.g., being embedded into or attached to the shaft, preferably, at or close to the distal end of the balloon dilation device. Alternatively, the shaft of the balloon dilation device 100 can be configured the same way as the shafts being described with respect to FIGS. 6, 7, 8, and 9, thus, having an inner and an outer hypo tube.

The hypo tube 110 is attached to a handle 112, the handle extending from the proximal end 114 of the balloon dilation device 100 towards the distal end 106 of the balloon dilation device 100. The central lumen extends through the handle 112 to an attachment 116 for inserting, e.g., a marker carrier (equipped with one or more sensor coils), a light fibre or a suction tube. The handle 112 has a length L1 of 130 mm and a diameter D1 of 19 mm.

The handle 112 comprises an attachment 118 for attaching a fluid source (not shown) to the balloon dilation device, e.g., via a tube. From the attachment 118, an inflation lumen (not visible) extends through the handle 112 and the shaft 108 to a connecting point (not visible) for feeding a fluid into or out of a balloon 102 that is arranged adjacent to the distal end 106 of the balloon dilation device 100. The balloon 102 can be inflated by feeding a fluid through the inflation lumen into the balloon 102. Respectively, the balloon 102 can be deflated by feeding a fluid out of the balloon 102 through the inflation lumen.

When being inflated, the balloon has a diameter D2 of 6 mm. In other embodiments that are not shown the diameter of the balloon in its inflated state can be different, e.g., the diameter can lie between 3 mm and 10 mm. The balloon 102 is fixedly arranged at the shaft 108 and has a length L2 of 18 mm. In various embodiments, however, the balloon can have a different length that, e.g., is between 10 mm and 25 mm, preferably, between 15 mm and 20 mm.

The shaft 108 has a length L3 of 128 mm. Extending from the distal end 106 of the balloon dilation device 100 towards the proximal end 114 of the balloon dilation device 100, the shaft 108 comprises a malleable tip region 122 having a length L4 of 30 mm. Preferably, the malleable tip region 122 of the shaft 108 is produced by heat treatment of the shaft 108.

A balloon dilation device having a shaft with a length of 128 mm can also have a malleable tip region having different length, e.g., a length that is between 10 mm and 60 mm, preferably between 20 mm and 50 mm, even more preferably between 25 mm and 35 mm. The balloon dilation device can also have a shaft having a different length, e.g., a length of between 1.2 mm and 1.8 mm, preferably between 1.2 mm and 1.6 mm, even more preferably between 1.2 mm and 1.4 mm. A balloon dilation device having a shaft with a length of between 1.2 mm and 1.8 mm can also have a malleable tip region extending from the distal end of the balloon dilation device towards the proximal end of the balloon dilation device, the malleable tip region having a length that is between 10 mm and 60 mm.

Since the balloon dilation device 100 is equipped with the sensor coil, position and orientation of the balloon dilation device 100 can be determined with a position detection system (not shown). In particular, position and orientation of the balloon dilation device 100 can be calculated using a determined position and orientation of the sensor coil. Therefore, the balloon dilation device 100 is exposed to an alternating electromagnetic field such that a current is induced in the sensor coil. The current induced depends on position and orientation of the sensor coil in relation to the alternating electromagnetic field. When a current is induced, a sensor coil signal is transmitted from the sensor coil to the position detection system, e.g., via a cable connecting the sensor coil to the position detection system. The sensor coil signal can be processed by the position detection system to determine position and orientation of the sensor coil. Having calculated position and orientation of the balloon dilation device based on the determined position and orientation of the sensor coil, the position of the balloon dilation device can be displayed in images of a patient for supporting a surgeon in navigating the balloon dilation device inside a human body.

Figure 2:
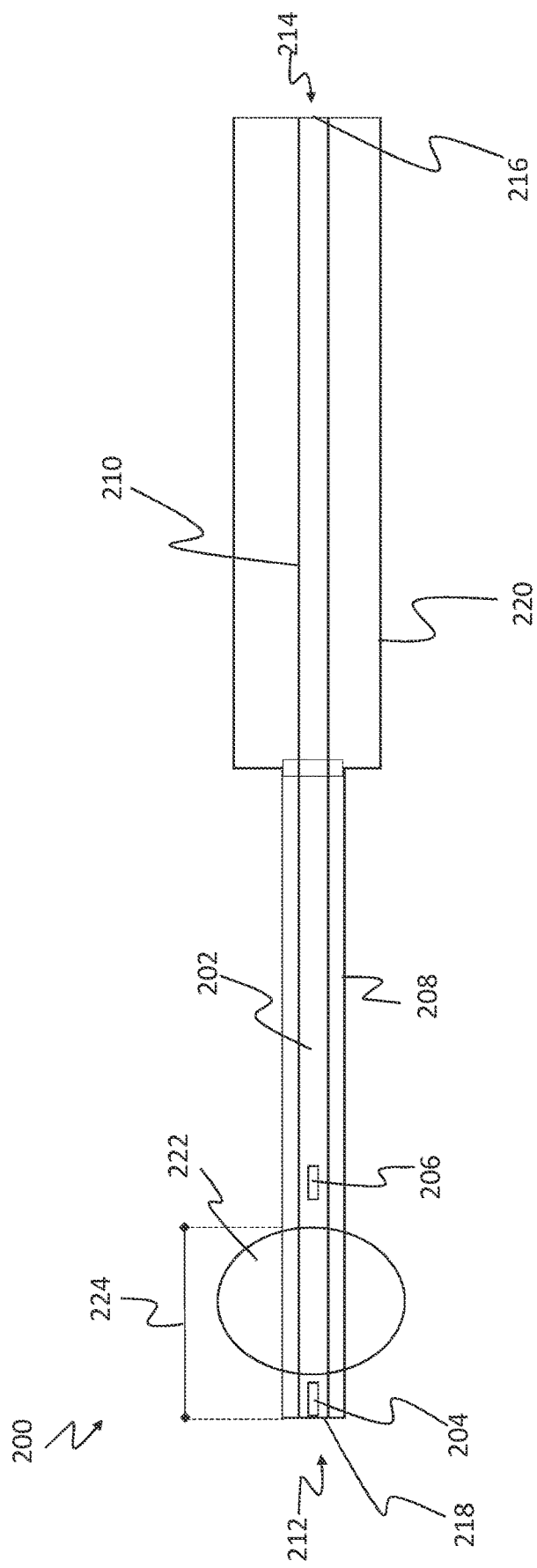
FIG. 2: schematically shows a balloon dilation device in a longitudinal sectional view with a marker carrier, the marker carrier having two sensor coils that are displaced in longitudinal direction along the shaft of the balloon dilation device.

FIG. 2 schematically shows a balloon dilation device 200 in a longitudinal sectional view with a marker carrier 202, the marker carrier 202 comprising two sensor coils 204, 206 that are displaced in longitudinal direction along the shaft 208.

The marker carrier 202 is arranged in a central lumen 210, the central lumen 210 extending from the distal end 212 of the balloon dilation device 200 to the proximal end 214 of the balloon dilation device 200. The marker carrier 202 extends through the full length of the central lumen 210 and can be removed from the lumen through an opening 216 at the proximal end 214 of the balloon dilation device 200, e.g., after having positioned the balloon dilation device 200, e.g., in a sinus cavity. Because the central lumen 210 also has an opening 218 at the distal end of the balloon dilation device 200, after removing the marker carrier 202 the central lumen 210 can be used for suction or irrigation purposes. For example, after removing the marker carrier 202 from the central lumen a suction tube can be inserted into the central lumen 210 for drainage of mucus from the paranasal sinuses. The central lumen 210 extends through the shaft 208 and through the handle 220 from the distal end 212 of the balloon dilation device 200 to the proximal end 214 of the balloon dilation device 200. By way of example, the shaft can comprise one hypo tube as described with reference to FIG. 1 or can have an inner and an outer hypo tube as described with reference to FIG. 5, 6, 7, 8, or 9.

Furthermore, an inflation lumen (not shown) extends from the proximal end 214 of the balloon dilation device 200 to a connecting point (not shown). At the connecting point the inflation lumen is fluidly connected to a balloon 222 that is arranged at the shaft 208. Through the inflation lumen a fluid can be fed into or out of the balloon for inflating and deflating the balloon 222, respectively.

The balloon 222 is arranged within a malleable tip region 224 of the shaft 208. In the malleable tip region, the shaft can be plastically deformed to facilitate accessing passageways and positioning of the balloon dilation device 200, e.g., in sinus cavities.

The first sensor coil 204 is arranged at the distal end 212 of the balloon dilation device 200 such that when the shaft is plastically deformed in the malleable tip region 224, e.g., using a shaping tool, the sensor coil 204 is displaced with respect to the rest of the shaft.

The second sensor coil 206 is arranged at the shaft but adjacent to the malleable tip region 224. Hence, if the shaft 208 is bend in the malleable tip region 224, the second sensor coil 206 is not displaced with respect to the rest of the shaft 208. Position and orientation of the second sensor coil thus represent position and orientation of the part of the shaft that stays unbend. However, when plastically deforming the shaft in the malleable tip region 224, the first 204 sensor coil is displaced with respect to the second sensor coil 206 such that the two sensor coils 204, 206 have a non-zero angle enclosed between their longitudinal axis.

By determining position and orientation of the first and second sensor coils 204, 206, the degree of bending of the shaft 208 can be calculated from the determined position and orientation of each of the two sensor coils 204, 206. In particular, the shape of the balloon dilation device in that section of the shaft that lies between the two sensor coils 204, 206 can be reconstructed based on the determined position and orientation of each of the two sensor coils 204, 206. Using the reconstructed shape of the balloon dilation device, the balloon dilation device 200 can be visualized on monitor in its actual shape thus having a bend malleable tip region 224.

This is of advantage since a surgeon can decide more reliably when to inflate or deflate the balloon 222 inside a sinus cavity based on the actual position and shape of the balloon dilation device 200 positioned inside, e.g., a sinus cavity.

Figure 3:
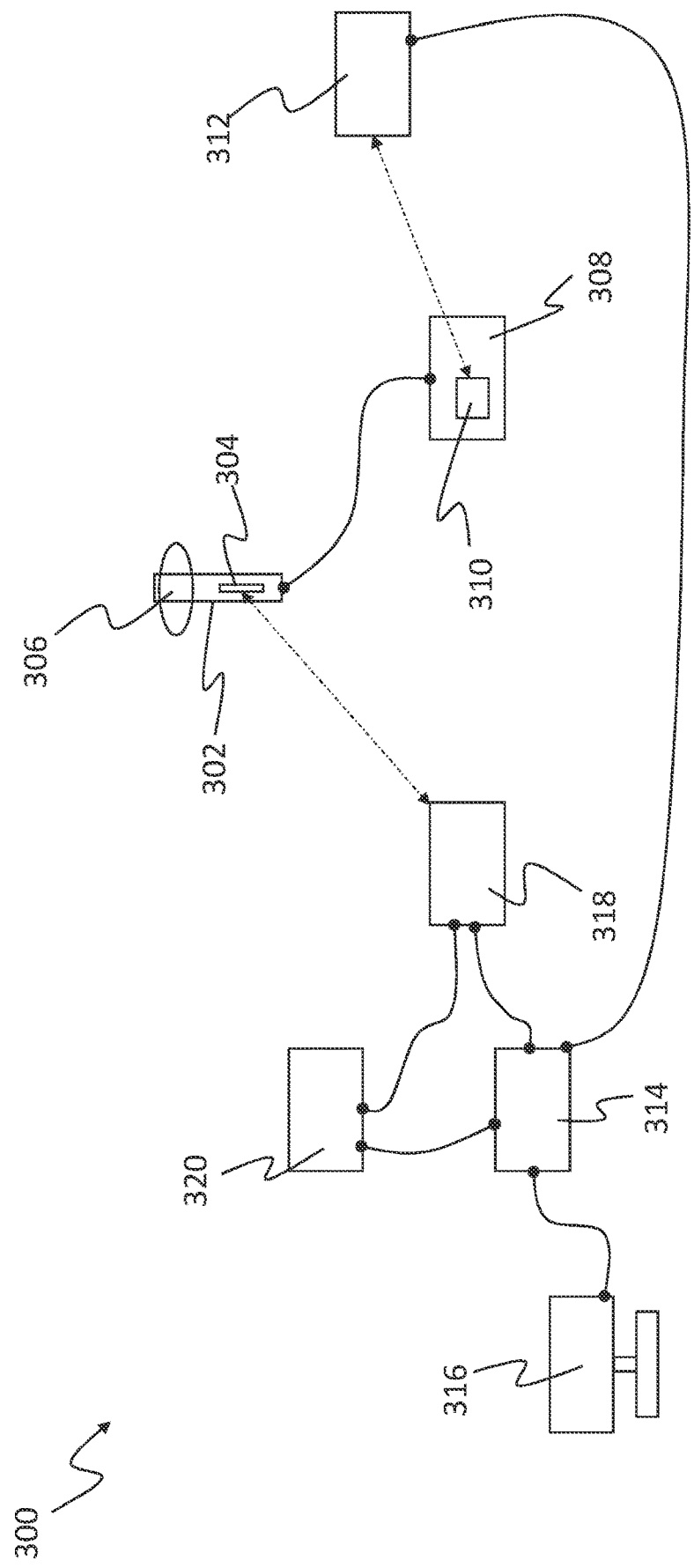
FIG. 3: schematically shows a medical system comprising a balloon dilation device that has a sensor coil and a balloon.

FIG. 3 schematically shows a medical system 300 comprising a balloon dilation device 302, the balloon dilation device 302 comprising a sensor coil 304 and a balloon 306.

The balloon dilation device 302 can be configured the same way as the balloon dilation device described with reference to FIG. 1 or the balloon dilation device described with reference to FIG. 2 or the balloon dilation device as described with reference to FIG. 5.

The balloon dilation device 302 is connected to a fluid source 308 via a tube. The fluid source is configured for providing a fluid, i.e., a gas or a liquid. For inflating the balloon 306, a fluid is fed into the balloon 306. The fluid source 308 comprises an optional fluid sensor 310 for measuring a physical quantity of a fluid that is fed into the balloon. The fluid sensor can be an inflation pressure sensor for measuring an inflation pressure or a fluid volume sensor for measuring an amount of fluid that has been fed into or out of the balloon. Also both sensors can be present at the same time. Additionally or alternatively to one or more fluid sensors comprised by the fluid source, the balloon dilation device itself can have one or more fluid sensors. These fluid sensor of the balloon dilation device can likewise be an inflation pressure sensor or a fluid volume sensor. The balloon dilation device can also comprise a sensor that is configured for directly detecting the shape of the balloon. Fluid sensor 310 of the fluid source 308 and, if present, fluid sensors comprised by the balloon dilation device 302 itself are configured for providing fluid sensor signals representing the measured a physical quantity of the fluid.

Fluid sensor signals representing a measured physical quantity of the fluid can be transmitted to a balloon shape computation unit 312, e.g., via a cable or wireless. The balloon shape computation unit 312 is configured for computing the shape of the balloon 306 based on fluid sensor signals provided by the fluid sensor 310 of the fluid source 308. If no fluid sensor 310 for measuring a physical quantity of the fluid is present in the medical system 300, also no balloon shape computation unit 312 needs to be present which is thus an optional element.

The balloon shape computation unit 312 is connected to a visualization unit 314, the visualization unit 314, preferably, being configured to access and use the computed balloon shape. Thus, the visualization unit 314 is configured to process the computed balloon shape, in particular, for visualizing the balloon dilation device 302 having a balloon shape as computed by the balloon shape computation unit 308 on a monitor 316.

The medical system 300 comprises a position detection system 318 for determining position and orientation of the balloon dilation device 302 based on sensor coil signals provided by the sensor coil 304 Preferably, the sensor coil 304 is arranged at the shaft of the balloon dilation device 302 at the distal end of the balloon dilation device 302. The position detection system 318 can comprise a field generator (not shown) for generating an alternating electromagnetic field. For determining position and orientation of the balloon dilation device 302, the balloon dilation device 302 equipped with the sensor coil 304 is exposed to the alternating electromagnetic field such that a current is induced in the sensor coil 304. When a current is induced, respective a sensor coil signal can be transmitted to the position detection system 318, e.g., via a cable or wirelessly. The position detection system 318 is configured for processing a received sensor coil signal for calculating position and orientation of the balloon dilation device 302. This often includes that position and orientation represented by the sensor coil signal are determined and used together with transformation functions obtained by calibrating the sensor coil to the tip of the balloon dilation device 302 to calculate position and orientation of the balloon dilation device 302 relative to the position detections system 318.

The position detection system 318 is connected to the visualization unit 314. The visualization unit 314 is configured for visualizing a digital representation of at least a part of the balloon dilation device 302, e.g., the balloon dilation device tip, on the monitor 316 based on the position and orientation of the balloon dilation device 302 as determined by the position detection system 318. Preferably, a digital representation of the balloon dilation device 302 is visualized together with images of a patient to support a surgeon in handling the balloon dilation device 302 while guiding the balloon dilation device 302 inside the human body.

In particular, if the balloon dilation device 302 comprises several sensor coils, preferably, at least two sensor coils, arranged at and distributed along the length of the shaft of the balloon dilation device 302, the medical system can comprise an optional device shape reconstruction unit 320. The device shape reconstruction unit 320 is connected to the position detection system 318 and to the visualization unit 314. The device shape reconstruction unit 320 is configured for reconstructing the shape of the balloon dilation device 302 based on position and orientation of the sensor coil 304 determined by the position detection system 318. In particular, the device shape reconstruction unit 320 is configured for accessing the determined position and orientation for each sensor coil present in the balloon dilation device 302 and to process the determined positions and orientations of the sensor coils for reconstructing the shape of the balloon dilation device 302.

Preferably, if a device shape reconstruction unit 320 is present, the visualization unit 314 is configured for visualizing the balloon dilation device 302 in its reconstructed shape. In particular, the shape of the balloon dilation device can be reconstructed taking into account a possible bending of the shaft in its malleable tip region.

Figure 4:
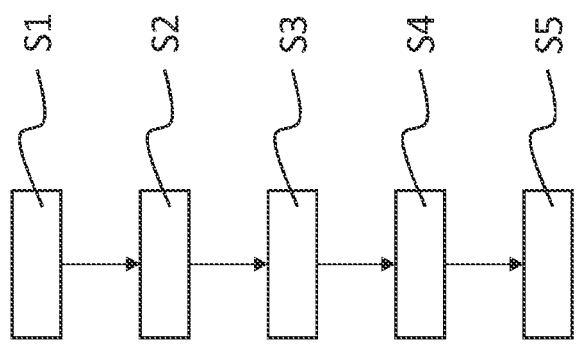
FIG. 4: shows a flow diagram representing a method for determining position and orientation of a balloon dilation device.

FIG. 4 shows a flow diagram representing a method for determining position and orientation of a balloon dilation device. The method described in the following can be implemented using a medical system as described with reference to FIG. 3.

The method comprises the steps of
generating an electromagnetic field S1,
exposing the balloon dilation device to the electromagnetic field, the balloon dilation device having an inflatable balloon and at least one sensor coil S2,
detecting position and orientation of the at least one sensor coil S3,
determining position and orientation of the balloon dilation device based on the detected position and orientation of the at least one sensor coil S4, and
visualizing a digital representation of at least a part of the balloon dilation device on a monitor based on the determined position and orientation of the balloon dilation device S5.

Figure 5:
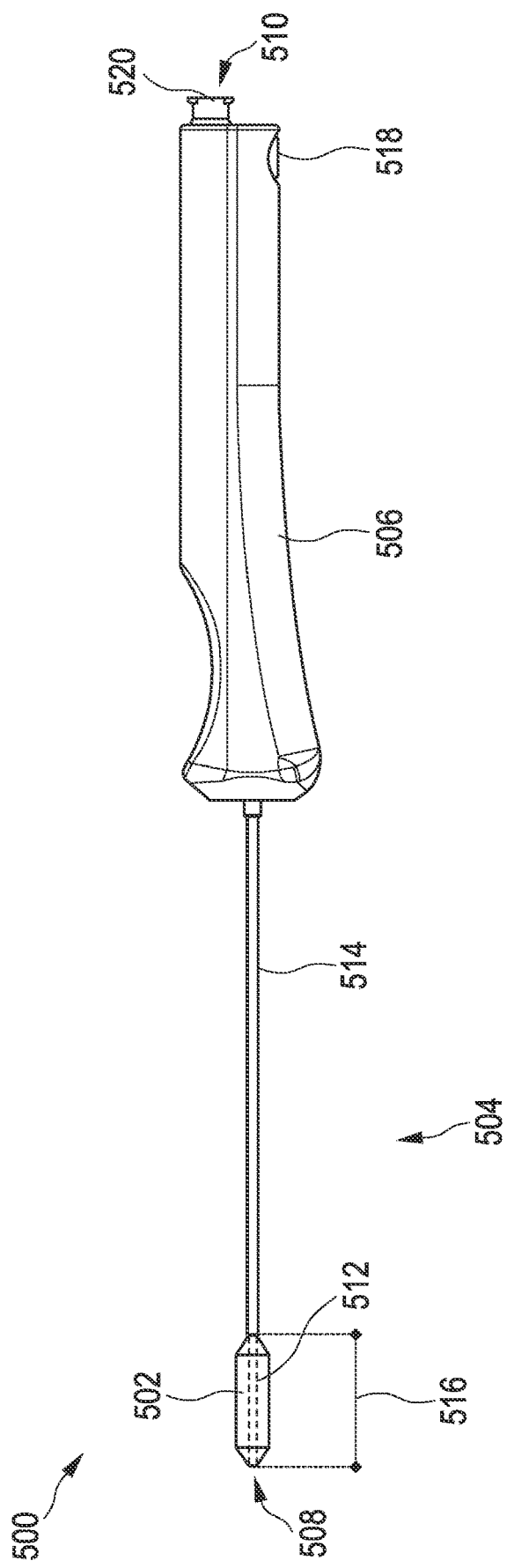
FIG. 5: schematically shows a balloon dilation device having a shaft comprising an inner and an outer hypo tube.

FIG. 5 shows a balloon dilation device 500 comprising a balloon 502, a shaft 504, a handle 506 and at least one sensor coil (not shown).

The shaft 504 extends from the distal end 508 of the balloon dilation device 500 towards the proximal end 510 of the balloon dilation device 500 and has an inflation lumen (not visible). The shaft 504 comprises an inner hypo tube 512 and an outer hypo tube 514. The inner hypo tube 512 has an outer diameter that is equal to or smaller than the diameter of a lumen of the outer hypo tube 514. The inner hypo tube 512 is at least partly arranged inside the lumen of the outer hypo tube 514. At least with the outer hypo tube 514, the shaft 504 is attached to the handle 506. The outer hypo tube 514 does not extend up to the distal end 508 of the balloon dilation device 500 but ends before. The inner hypo tube 512 extends up to the distal end 508 of the balloon dilation device 500. The total length of the shaft 504 thus is the sum of the lengths of the visible part of the outer hypo tube 514 and the visible part of the inner hypo tube 512.

The inner hypo tube 512 is completely annealed such that it has an ultimate tensile strength of up to 750 N/mm$^2$. That part of the inner hypo tube 512 that extends between the distal end 508 of the balloon dilation device 500 and the distal end of the outer hypo tube 514, i.e., the visible part of the inner hypo tube 512, forms a malleable tip region 516 of the shaft.

In the malleable tip region 516 the inflatable balloon 502 is fixedly arranged at the shaft 504, i.e., attached to the inner hypo tube 512 of the shaft 504. The balloon 502 has a length that is approximately equal to the length of the malleable tip region 516. Thereby, when plastically deforming the shaft 504 in the malleable the region 516, the balloon 502 itself also deforms accordingly. In particular, if the malleable tip region 516 is formed to have an angle, typically, the balloon 502, too, shows a corresponding bend.

The balloon 502 is fluidly connected to the inflation lumen of the balloon dilation device 500 such that the balloon 502 can be inflated and deflated by feeding a fluid through the inflation lumen into or out of the balloon 502. The fluid for inflating the balloon 502 can be provided by a fluid source (not shown) that is connect to the inflation lumen, e.g., via a tube, at the attachment 518 arranged at the handle 506. The inflation lumen thus extends from the attachment 518 through the handle 506 and the shaft 504 to a connecting point (not visible) for feeding a fluid into or out of a balloon 502.

The balloon dilation device 500 comprises a central lumen (not visible). The central lumen extends from an opening of the inner hypo tube 512 at the distal end 508 of the balloon dilation device 500 to an attachment 520 that is arranged at the handle 506. Alternatively, the central lumen can extend from the attachment 520 through the handle 506 and the shaft and end before the distal end 508 of the balloon dilation device 500. In that embodiment the shaft can be closed at the distal end 508 of the balloon dilation device 500, i.e., in this case no opening is present at the distal end 508 of the balloon dilation device 500.

In the central lumen at least one sensor coil (not shown) is arranged that is configured for capturing an electromagnetic field and for providing a sensor coil signal representing position and orientation of the sensor coil. By means of the at least one sensor coil, the balloon dilation device 500 can be connected to a position detection system that is configured for determining position and orientation of the balloon dilation device 500 in an electromagnetic field.

The at least one sensor coil can also be comprised in a marker carrier that is arranged inside the central lumen of the balloon dilation device 500. In particular, through the attachment 520, a marker carrier comprising, e.g., two sensor coils can be inserted into the central lumen to be removably arranged inside the central lumen.

If a marker carrier comprises at least one sensor coil that is configured for capturing an electromagnetic field, position and orientation of the sensor coil can be determined with an electromagnetic position detection system. In particular, the at least one sensor coil of a marker carrier can be used to connect the balloon dilation device 500 to a position detection system in order to track the position of the balloon dilation device 500. By connecting the balloon dilation device 500 to a position detection system, it is possible to display the position of the balloon dilation device 500 in sectional images of a model of a patient in order to assist a surgeon in navigating the balloon dilation device 500. Since the marker carrier can be arranged removably inside the central lumen, after having positioned the balloon dilation device 500 in a cavity, the marker carrier can be removed from the central lumen and, e g., a suction tube can be inserted into the central lumen.

If a marker carrier comprising sensor coils is arranged inside the central lumen, preferably, one sensor coil is arranged at the distal end 508 of the at least balloon dilation device 500 and a second coil is arranged adjacent to the malleable tip region 516, i.e., in that part of the shaft 504 in which the outer hypo tube 514 is present. Preferably, the sensor coils of the marker carrier are arranged inside the central lumen such that, if the malleable tip region of the shaft is deformed plastically, a non-zero angle is enclosed between the longitudinal axis of the two coils. From the determined position and orientation of the two sensor coils with respect to each other, it is possible to determine a bending of the shaft 504, in particular, in the malleable tip region 516 and to reconstruct the shape of the balloon dilation device 500 having a shaft with a plastically deformed malleable tip region.

Figure 6:
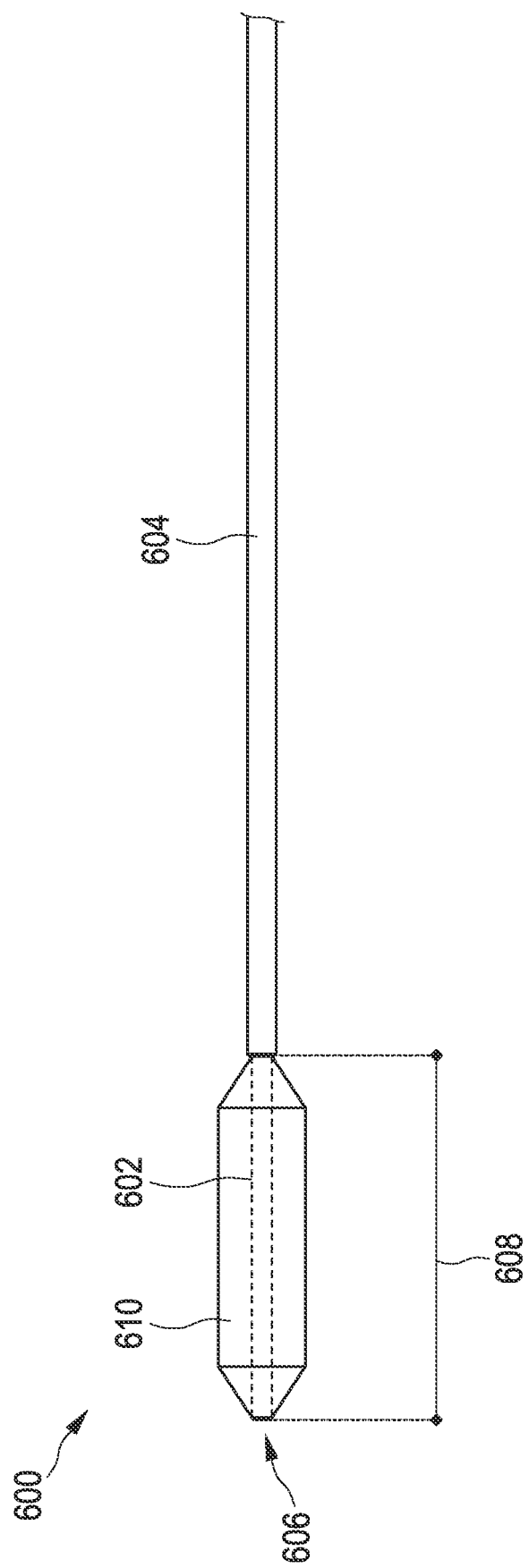
FIG. 6: schematically shows a shaft of a balloon dilation device, the shaft comprising an inner and an outer hypo tube.

FIG. 6 shows a shaft 600 that has an inner hypo tube 602 and an outer hypo tube 504. The shaft 600 can be attached to a handle (not shown) of a balloon dilation device, e.g., of a balloon dilation device as described with respect to FIG. 1 or of a balloon dilation device as described with respect to FIG. 5.

The inner hypo tube 602 is completely annealed. The outer hypo tube 604 is configured such that it does not plastically deform if an external force of a magnitude typically acting on the shaft during surgery is exerted on the outer hypo tube 604. The inner hypo tube 602 is at least partly arranged inside a lumen of the outer hypo tube 604.

The outer hypo tube 604 ends before the distal end 606 of the shaft 600. The inner hypo tube 602 extends up to the distal end 606 of the shaft 600 such that the shaft's total length is the sum of the visible parts of the inner hypo tube 602 and the outer hypo tube 604.

That part of the inner hypo tube 602 that extends from the distal end of the outer hypo tube 604 to the distal end 606 of the shaft 600 forms a malleable tip region 608 of the shaft 600. In particular, in the malleable tip region 608, the shaft can be plastically deformed, e.g., using a shaping tool. It is preferred that prior surgery, the shaft in its malleable tip region 608 is plastically deformed so that the shape of the shaft is suitable for a specific procedure to be carried out with a balloon dilation device.

For example, for different procedures in the malleable tip region 608 the shaft 600 can be plastically deformed to have a specifically selected angle with respect to the rest of the shaft, i.e., with respect to the outer hypo tube 604. For example, a shaping tool can be used having several pre-fixed shape positions that are suitable, e.g., for accessing a particular cavity.

Fixed to the shaft 600 in the malleable tip region 608 there is an inflatable balloon 610. The balloon 610 has a length that corresponds to the length of the malleable tip region 608. The balloon 610 is fluidly connected to the inflation lumen (not visible) of the shaft 600 such that the balloon 610 can be inflated and deflated by feeding a fluid through the inflation lumen into or out of the balloon 600.

At the shaft 600, at least one sensor coil (not visible) is arranged, the at least one sensor coil being configured for capturing an electromagnetic field and for providing a sensor coil signal representing position and orientation of the sensor coil in an electromagnetic field. For example, the shaft 600 can comprise two sensor coils that are arranged at the shaft 600 as described with reference to FIG. 7.

Figure 7:
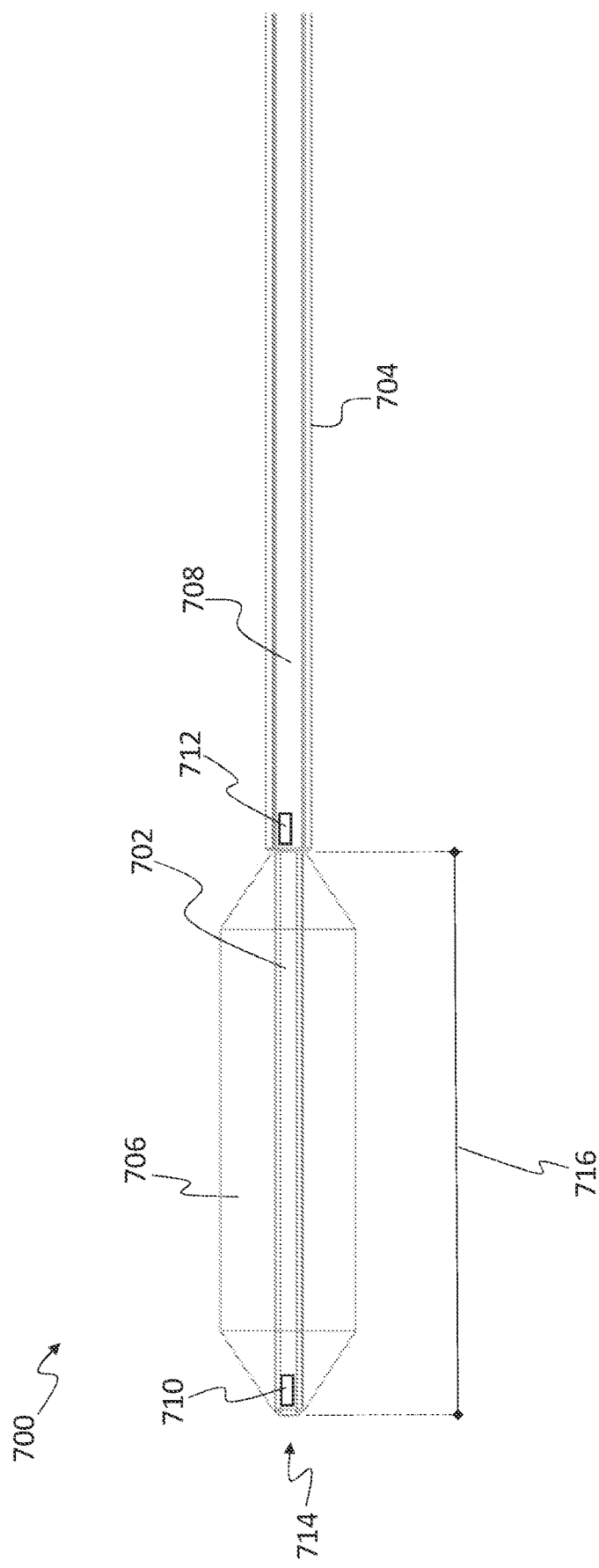
FIG. 7: schematically shows a shaft of a balloon dilation device in a longitudinal sectional view, the shaft comprising an inner and an outer hypo tube.

In FIG. 7, a shaft 700 is shown in a longitudinal sectional view, the shaft 700 having an inner hypo tube 702 and an outer hypo tube 704 that are arranged and configured as described with reference to FIG. 6. Also as described with reference to FIG. 6 there is a balloon 706 fixedly arranged at the shaft 700.

The shaft 700 has a central lumen 708 and an inflation lumen (not visible). In the central lumen 708 two sensor coils 710, 712 are arranged. The first sensor coil 710 is arranged at the distal end 714 of the shaft 700 and the second sensor coil 712 is arranged adjacent to the malleable tip region 716 of the shaft 700. If the malleable tip region 716 is plastically deformed to have an angle with respect to the rest of the shaft 700, preferably, the two sensor coils are displaced such that their longitudinal axis enclose a non-zero angle.

Each of the sensor coils 710, 712 is connected to electrical wiring (not shown) running from the respective sensor coil 710, 712 towards a proximal end of the shaft 700. Preferably, if the shaft 700 is attached to a handle of a balloon dilation device, the electrical wiring run up to an electrical connection of the balloon dilation device at which the electrical wiring can be connected to a cable for connecting the balloon dilation device to a position detection system. Via the electrical wiring, sensor coil signals provided by the sensor coils 710, 712 can be transmitted to a position detection system that is configured for determining position and orientation of each of the sensor coils 710, 712 by analysing respective sensor coil signals. Based on determined position and orientation of the two sensor coils it is possible to determine the bending of the shaft 700 and to reconstruct the actual shape of the shaft 700 in case the malleable tip region 716 of the shaft 700 is plastically shaped.

The sensor coils 710, 712 can be part of a marker carrier that is removably arranged inside the central lumen 708 of the shaft 700 to connect a balloon dilation device to a position detection system.

It is also possible that the shaft comprises only one of the sensor coils 710, 712 or additional sensor coils that are distributed along the length of the shaft.

Figure 8:
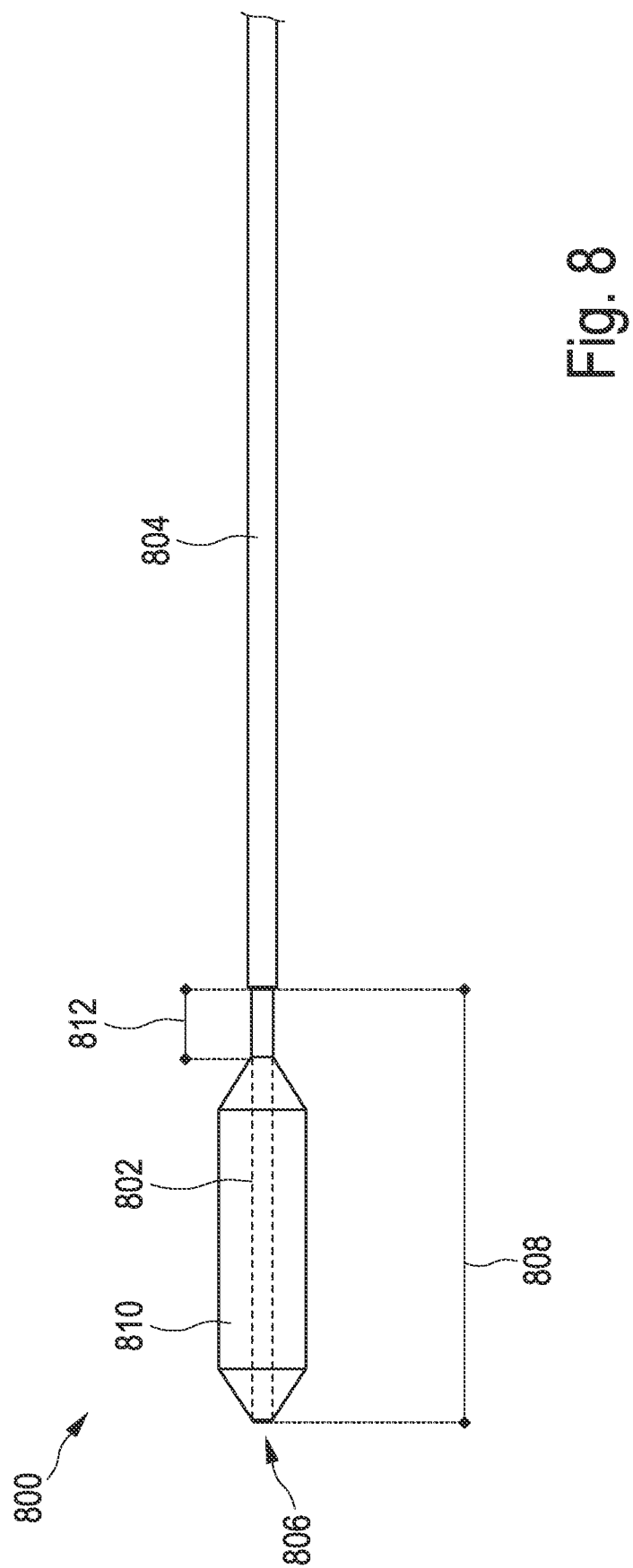
FIG. 8: schematically shows a shaft of a balloon dilation device, the shaft comprising an inner and an outer hypo tube.

In FIG. 8, a shaft 800 is shown having a completely annealed inner hypo tube 802 and an outer hypo tube 804. The outer hypo tube 804 is configured such that it does not plastically deform if an external force of a magnitude typically acting on the shaft 800 during surgery is exerted on the outer hypo tube 804. The shaft 800 can be attached to a handle (not shown) of a balloon dilation device, e.g., of a balloon dilation device as described with reference to FIG. 1 or of a balloon dilation device as described with reference to FIG. 5.

The inner hypo tube 802 is arranged at least partly in a lumen of the outer hypo tube 804. The outer hypo tube 804 ends before the distal end 806 of the shaft 800. The completely annealed inner hypo tube 802 extends up to the distal end 806 of the shaft 800 and that part of the inner hypo tube 802 that extends from the distal end of the outer hypo tube 804 to the distal end 806 of the shaft 800 forms the malleable tip region 808 of the shaft 800.

In the malleable tip region 808, a balloon 810 is fixedly arranged at the shaft 800. The balloon 810 is fluidly connected to the inflation lumen (not visible) of the shaft 800 such that the balloon 810 can be inflated and deflated by feeding a fluid through the inflation lumen into or out of the balloon 800.

The balloon 810 is arranged adjacent to the distal end 806 of the shaft and has a length that is smaller than the length of the malleable tip region. As a result, the proximal end of the balloon 810 ends before proximal end of the malleable tip region 808 such that there is an exposed section 812 of the inner hypo tube 802 in which no balloon 810 is arranged. Preferably, this exposed section 812 of the inner hypo tube 802 forms a bending section in which the malleable tip region 808 can be plastically deformed several times for shaping the malleable tip region 808.

If the malleable tip region 808 is deformed in the exposed section 812 such that the malleable tip region 808 has an angle to the rest of the shaft 800, i.e., to the outer hypo tube 804, the remaining part of the malleable tip region 808 in which the balloon 810 is arranged can maintain its shape. Advantageously, thereby, the balloon 810 itself is not mechanically stressed by shaping the malleable tip region 808 and can maintain its balloon shape.

At the shaft 800, at least one sensor coil (not visible) is arranged. For example, the shaft 800 can comprise two sensor coils that are arranged at the shaft 800 as described with reference to FIG. 9.

FIG. 9 shows a shaft 900 in a longitudinal sectional view, the shaft 900 having a completely annealed inner hypo tube 902 and an outer hypo tube 904 that are arranged and configured as described with reference to FIG. 8.

The shaft 900 has a central lumen 906 and an inflation lumen (not visible). In the central lumen 906 two sensor coils 908, 910 are arranged such that a first coil 908 is arranged at the distal end 912 of the shaft 900 and a second coil 910 is arranged adjacent to the malleable tip region 914. The two sensor coils 908, 910 are connected to electrical wiring (not shown) for connecting the two sensor coils 908, 910 to a position detection system. From sensor coil signals provided by the sensor coils 908, 910, position and orientation of each of the sensor coils can be determined with a connected position detection system.

In the malleable tip region 914, a balloon 916 is fixedly arranged at the shaft 900 and fluidly connected to the inflation lumen such that the balloon 916 can be inflated and deflated by feeding a fluid through the inflation lumen into or out of the balloon 916.

As described with reference to FIG. 8, the balloon 912 is arranged adjacent to the distal end 912 of the shaft 900 and ends before the distal end of the outer hypo tube 904. Thereby, a section 918 of the inner hypo tube 902 that extends between the proximal end of the balloon 916 and the proximal end of the malleable tip region 914 is exposed, i.e., is visible from outside. In particular, in the exposed section 918, the shaft can be plastically deformed to shape the malleable tip region 914 to have an angle to the rest of the shaft 900.

The invention claimed is:

1. A system comprising:
    a balloon dilation device, the balloon dilation device comprising a shaft having an inflation lumen and a malleable region, the malleable region comprising a distal end, an inflatable balloon fixedly arranged at the shaft such that the inflatable balloon cannot be shifted along the shaft in a longitudinal direction, at least one sensor coil at the malleable region distal end, and at least a second sensor coil that is arranged at the shaft at a non-zero angle to the at least one sensor coil, wherein when the malleable region is formed to have an angle, the balloon comprises a corresponding bend;
    a navigation system comprising a field generator configured to generate an alternating electromagnetic field, the navigation system configured to determine a position and an orientation of the balloon dilation device based on sensor coil signals provided by the at least one sensor coil and the at least second sensor coil of the balloon dilation device when the at least one sensor coil and the at least second sensor coil are exposed to the alternating electromagnetic field, wherein the navigation system is further configured to determine a shape of a portion of the balloon dilation device based on the position and orientation of the at least one sensor coil and the at least second sensor coils, whereby the shape of the portion of the balloon dilation device that lies between the at least one sensor coil and the at least second sensor coils is determined; and
    a fluid source attached to the balloon dilation device for feeding a fluid into the balloon.

2. The system of claim 1, further comprising a monitor configured to visualize at least part of the balloon dilation device.

3. The system of claim 1, wherein the fluid source comprises at least one fluid sensor for measuring a physical quantity of the fluid provided by the fluid source and for providing fluid sensor signals representing the measured physical quantity.

4. The system of claim 1, wherein the shaft further comprises a central lumen having a distal end.

5. The system of claim 4, wherein the central lumen has an opening at the distal end.

6. The system of claim 5, wherein the central lumen comprises a light fiber therein.

7. The system of claim 4, wherein the balloon dilation device further comprises a marker carrier that is removably arranged inside and extends along a length of the central lumen, wherein the marker carrier comprises the at least one sensor coil.

8. The system of claim 1, wherein the balloon dilation device further comprises a handle.

9. The system of claim 1, wherein the inflatable balloon is attached to the shaft of the balloon dilation device in the malleable region.

10. The system of claim 1, wherein the at least second sensor coil is displaced at a distance in the longitudinal direction from the at least one sensor coil.

11. The system of claim 1, wherein the at least second sensor coil is arranged at the shaft adjacent to the malleable region.

12. The system of claim 1, wherein the malleable region of the shaft has a length between about 10 mm and about 60 mm.

13. The system of claim 12, wherein the malleable region of the shaft has a length between about 20 mm and about 50 mm.

14. The system of claim 13, wherein the malleable region of the shaft has a length between about 25 mm and about 35 mm.

15. The system of claim 1, wherein the malleable region of the shaft is made from a material having an ultimate tensile strength of up to 720 $Nmm^{-2}$.

* * * * *